United States Patent

Gallenkamp et al.

Patent Number: 5,675,016
Date of Patent: Oct. 7, 1997

[54] PROCESS FOR THE PREPARATION OF 1,3-DIMETHYL-5-FLUORO-PYRAZOLE-4-CARBOXANILIDES

[75] Inventors: Bernd Gallenkamp; Lothar Rohe, both of Wuppertal; Albrecht Marhold, Leverkusen, all of Germany

[73] Assignee: Bayer Aktiengesellschaft, Leverkusen, Germany

[21] Appl. No.: 755,678

[22] Filed: Nov. 25, 1996

[30] Foreign Application Priority Data

Dec. 1, 1995 [DE] Germany ................ 195 44 800.6

[51] Int. Cl.$^6$ ................................. C07D 231/16
[52] U.S. Cl. .................................... 548/374.1
[58] Field of Search ......................... 548/374.1

[56] References Cited

U.S. PATENT DOCUMENTS

| | | | |
|---|---|---|---|
| 4,742,074 | 5/1988 | Nishida et al. | 548/374.1 |
| 4,792,565 | 12/1988 | Shimotori et al. | 548/374.1 |
| 5,223,526 | 6/1993 | McLoughlin et al. | |

FOREIGN PATENT DOCUMENTS

| | | |
|---|---|---|
| 0 199 822 | 11/1986 | European Pat. Off. . |
| 665598 | 9/1938 | Germany . |
| 63-48269 | 2/1988 | Japan . |

OTHER PUBLICATIONS

H.C. Fielding et al., Journal of Fluorine Chemistry, vol. 59, pp. 15–31 (1992).

M. Tordeux et al., Synthetic Communications, vol. 12, No. 7, pp. 513–520 (1982).

L.F. Lee et al., J. Heterocyclic Chem., vol. 22, pp. 1621–1630 (1985).

Chemical Abstracts, vol. 113, Abstract No. 113:78387c, p. 784 (1990).

Primary Examiner—Robert W. Ramsuer
Attorney, Agent, or Firm—Sprung Kramer Schaefer & Briscoe

[57] ABSTRACT

A new process for the preparation of a known 1,3-dimethyl-5-fluoro-pyrazole-4-carboxanilide of the formula

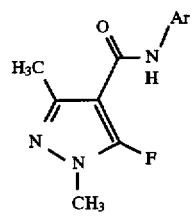

in which
Ar represents optionally substituted phenyl,
which process comprises
a) reacting in a first stage, 1,3-dimethyl-5-chloropyrazole-4-carbonyl chloride with a fluoride, if appropriate in the presence of a diluent, and
b) reacting in a second stage, the 1,3-dimethyl-5-fluoropyrazole-4-carbonyl fluoride obtained in this reaction with an aniline of the formula $$H_2N-Ar$$

in which
Ar has the abovementioned meaning,
if appropriate in the presence of an acid acceptor and if appropriate in the presence of a diluent.

1,3-Dimethyl-5-fluoro-pyrazole-4-carbonyl fluoride as a new compound.

9 Claims, No Drawings

PROCESS FOR THE PREPARATION OF 1,3-DIMETHYL-5-FLUORO-PYRAZOLE-4-CARBOXANILIDES

The present invention relates to a new process for the preparation of 1,3-dimethyl-5-fluoro-pyrazole-4-carboxanilides, which are known as active compounds having fungicidal properties. The invention furthermore also relates to 1,3-dimethyl-5-fluoro-pyrazole-4-carbonyl fluoride, which is new, and to its use as an intermediate product.

It has already been disclosed that certain 1,3-dimethyl-5-fluoro-pyrazole-4-carboxamides are accessible by fluorinating the corresponding 5-chloro-pyrazole derivatives (cf. EP-A 0 199 822). Thus, 1,3-dimethyl-N-(1,1-dimethyl-indan-4-yl)-5-fluoro-pyrazole-4-carboxamide is obtained by treatment of 1,3-dimethyl-N-(1,1-dimethyl-indan-4-yl)-5-chloro-pyrazole-4-carboxamide with potassium fluoride. A disadvantage of this process is that a product prepared by an expensive synthesis is employed as the starting substance. The fact that the yields of the desired compounds are relatively low is also unfavourable. Since high reaction temperatures are required, furthermore, only substances having heat-stable substituents can be prepared in this manner.

It has furthermore also already been disclosed that numerous 1-methyl-5-fluoropyrazole-4-carboxanilides can be synthesized starting from the corresponding 1-methyl-5-chloro-pyrazole-4-carbaldehydes (cf. WO 93-11 117). Thus, for example, 1,3-dimethyl-5-fluoro-pyrazole-4-carboxylic acid (2-cycloheptyl)-anilide is obtained by reacting 1,3-dimethyl-5-chloro-pyrazole-4-carbaldehyde with potassium fluoride, converting the 1,3-dimethyl-5-fluoro-pyrazole-4-carbaldehyde formed in this reaction into 1,3-dimethyl-5-fluoro-pyrazole-4-carboxylic acid with potassium dichromate, preparing 1,3-dimethyl-5-fluoro-pyrazole-4-carbonyl chloride from this compound by treatment with thionyl chloride, and reacting the latter product with 2-cycloheptyl-aniline. This synthesis can be illustrated by the following equation:

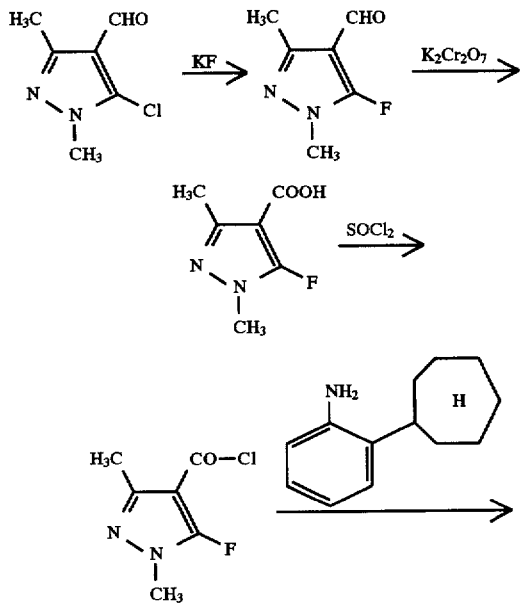

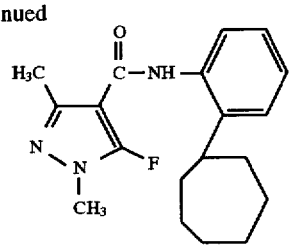

A decisive disadvantage of this process is that many reaction steps are necessary and the fluorination in the first stage proceeds in very low yields.

It has now been found that 1,3-dimethyl-5-fluoro-pyrazole-4-carboxanilides of the formula

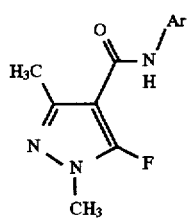

(I)

in which

Ar represents optionally substituted phenyl, are obtained by a process in which a) in a first stage, 1,3-dimethyl-5-chloro-pyrazole-4-carbonyl chloride of the formula

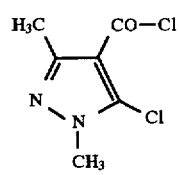

(II)

is reacted with fluorides, if appropriate in the presence of a diluent, and b) in a second stage, the 1,3-dimethyl-5-fluoro-pyrazole-4-carbonyl fluoride formed in this reaction, of the formula

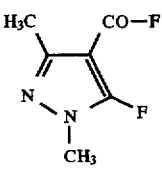

(III)

is reacted with anilines of the formula

H₂N—Ar    (IV)

in which

Ar has the abovementioned meaning, if appropriate in the presence of an acid acceptor and if appropriate in the presence of a diluent.

It is to be described as extremely surprising that 1,3-dimethyl-5-fluoro-pyrazole-4-carboxanilides can be prepared in a high yield and excellent purity by the process according to the invention. In fact, on the basis of the known prior art, it was to be expected that the fluorination would not be equally successful on the pyrazole ring and in the acid group. Furthermore, it was to be assumed that the acid fluoride is less reactive in the reaction with anilines than the corresponding acid chloride and the formation of the desired end products would therefore meet with difficulties. In contrast to expectations, however, this is not the case. Rather, the two-stage process proceeds without problems and without noticeable side reactions.

If 1,3-dimethyl-5-chloro-pyrazole-4-carbonyl chloride is reacted with potassium fluoride in the first stage and the 1,3-dimethyl-5-fluoro-pyrazole-4-carbonyl fluoride formed in this reaction is reacted with 2-cycloheptyl-aniline in the second stage, the course of the process according to the invention can be illustrated by the following equation:

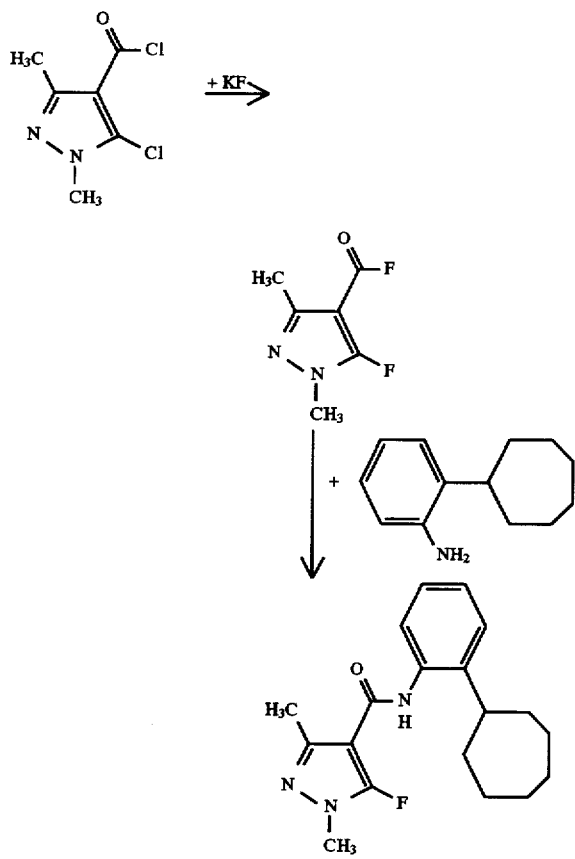

The 1,3-dimethyl-5-chloro-pyrazole-4-carbonyl chloride of the formula (II) required as the starting substance in carrying out the process according to the invention is known (cf. IP-A 1990 - 85 257 and Chem. Abstr. 113, 78 387).

Possible reaction components in carrying out the first stage of the process according to the invention are all the customary metal fluorides, ammonium fluoride and phosphonium fluorides. Alkali metal fluorides, such as potassium fluoride and caesium fluoride, and furthermore ammonium fluoride or triphenylmethylphosphonium fluoride, can preferably be used. The fluorides are known.

The 1,3-dimethyl-5-fluoro-pyrazole-4-carbonyl fluoride of the formula (III) formed in carrying out the first stage of the process according to the invention is new. It is used as the starting substance for carrying out the second stage of the process according to the invention.

Formula (IV) provides a general definition of the anilines required as reaction components for carrying out the second stage of the process according to the invention. In this formula, Ar preferably represents a grouping of the formula

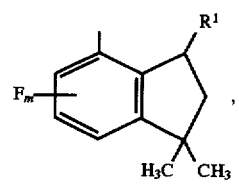

in which m represents 0 or 1 and $R^1$ represents hydrogen or methyl, or

Ar preferably represents a grouping of the formula

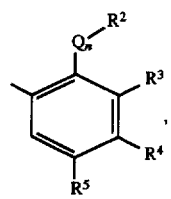

in which n represents 0 or 1,

Q represents alkylene having 1 to 3 carbon atoms, alkenylene having 2 or 3 carbon atoms or alkinylene having 2 or 3 carbon atoms, or represents a grouping of the formula —$(CH_2)_t$—CH=, in which t represents the numbers 0, 1, 2 or 3 and the —$(CH_2)_t$-unit is bonded to the phenyl ring, or represents a grouping of the formula —$(CH_2)_p$—Y—$(CH_2)_r$—, in which p and r independently of one another represent the numbers 0, 1 or 2 and Y represents oxygen or sulphur, the —$(CH_2)_p$-unit in each case being bonded to the phenyl ring, $R^2$ represents cycloalkyl having 3 to 12 carbon atoms which is optionally monosubstituted or polysubstituted in an identical or different manner by alkyl having 1 to 8 carbon atoms, alkoxy having 1 to 8 carbon atoms, halogen and/or cyano, or represents cycloalkenyl having 3 to 12 carbon atoms which is optionally monosubstituted or polysubstituted in an identical or different manner by alkyl having 1 to 8 carbon atoms, alkoxy having 1 to 8 carbon atoms, halogen and/or cyano, or represents bicycloalkyl having 6 to 12 carbon atoms which is optionally monosubstituted or polysubstituted in an identical or different manner by alkyl having 1 to 8 carbon atoms, alkoxy having 1 to 8 carbon atoms, halogen and/or cyano, or represents oxacycloalkyl having 2 to 12 carbon atoms which is optionally monosubstituted or polysubstituted in an identical or different manner by alkyl having 1 to 8 carbon atoms, alkoxy having 1 to 8 carbon atoms, halogen and/or cyano, or represents oxacycloalkenyl having 4 to 12 carbon atoms which is optionally monosubstituted or polysubstituted in an identical or different manner by alkyl having 1 to 8 carbon atoms, alkoxy having 1 to 8 carbon atoms, halogen and/or cyano, or represents thiacycloalkyl having 3 to 12 carbon atoms, which is optionally monosubstituted or polysubstituted in an identical or different manner by alkyl having 1 to 8 carbon atoms, alkoxy having 1 to 8 carbon atoms, halogen and/or cyano, or represents thiacycloalkenyl having 4 to 12 carbon atoms which is optionally monosubstituted or polysubstituted in an identical or different manner by alkyl having 1 to 8 carbon atoms, alkoxy having 1 to 8 carbon atoms, halogen and/or cyano, or represents azacycloalkyl having 2 to 12 carbon atoms which is optionally monosubstituted or polysubstituted in an identical or different manner by alkyl having 1 to 8 carbon atoms, alkoxy having 1 to 8 carbon atoms, halogen and/or cyano, the saturated or unsaturated ring in each case being divalent if —Q—$R^2$ represents —$(CH_2)_t$—CH=, and $R^3$, $R^4$ and $R^5$ independently of one another represent hydrogen, halogen, cyano, alkyl having 1 to 6 carbon atoms, alkenyl having 2 to 6 carbon atoms, alkinyl having 2 to 6 carbon atoms, alkoxy having 1 to 4 carbon atoms, alkylthio having 1 to 4 carbon atoms, cycloalkyl having 3 to 6 carbon atoms or halogenomethoxy.

Ar also particularly preferably represents a grouping of the formula

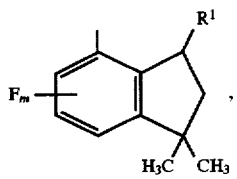

in which m represents 0 or 1 and $R^1$ represents hydrogen or methyl.

Furthermore

Ar also particularly preferably represents a grouping of the formula

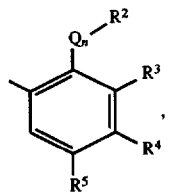

in which

Q preferably represents straight-chain or branched alkylene having 1 to 3 carbon atoms, alkenylene having 2 or 3 carbon atoms or alkinylene having 2 or 3 carbon atoms, or represents a grouping of the formula —$(CH_2)_t$—CH=, in which t preferably represents the numbers 0, 1 or 2, the —$(CH_2)_t$-unit in each case being bonded to the phenyl ring, or represents a grouping of the formula —$(CH_2)_p$—Y—$(CH_2)_r$—, in which p and r independently of one another represent the numbers 0, 1 or 2 and Y represents oxygen or sulphur, the —$(CH_2)_p$-unit in each case being bonded to the phenyl ring, n preferably represents the numbers 0 or 1, $R^2$ preferably represents cycloalkyl having 3 to 8 carbon atoms which is optionally monosubstituted to tetrasubstituted in an identical or different manner by alkyl having 1 to 4 carbon atoms, alkoxy having 1 to 4 carbon atoms, fluorine, chlorine, bromine and/or cyano, or represents cycloalkenyl having 3 to 8 carbon atoms which is optionally monosubstituted to tetrasubstituted in an identical or different manner by alkyl having 1 to 4 carbon atoms, alkoxy having 1 to 4 carbon atoms, fluorine, chlorine, bromine and/or cyano, or represents bicycloalkyl having 6 to 10 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, or represents oxacycloalkyl having 2 to 7 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, or represents oxacycloalkenyl having 4 to 7 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, or represents thiacycloalkyl having 3 to 7 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, or represents thiacycloalkenyl having 4 to 7 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, or represents azacycloalkyl having 2 to 7 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, the ring in the abovementioned radicals in each case being divalent if the grouping —Q—$R^2$ represents —$(CH_2)_t$—CH=, and $R^3$, $R^4$ and $R^5$ independently of one another represent hydrogen, fluorine, chlorine, bromine, cyano, alkyl having 1 to 4 carbon atoms, alkenyl having 2 to 4 carbon atoms, alkinyl having 2 to 4 carbon atoms, methoxy, ethoxy, methylthio, ethylthio, cyclopropyl, cyclopentyl, cyclohexyl, fluoromethoxy, difluoromethoxy, trifluoromethoxy, chloromethoxy, dichloromethoxy or trichloromethoxy.

Ar especially preferably represents a grouping of the formula

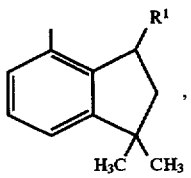

in which $R^1$ represents hydrogen or methyl.

Ar moreover especially preferably represents a grouping of the formula

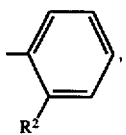

in which
R² represents cyclopentyl, cyclohexyl, cycloheptyl or bicyclo[2.2.1]-heptyl.

The anilines of the formula (IV) are known or can be prepared by known methods (compare WO 93-11 117).

Possible diluents for carrying out the first stage of the process according to the invention are all the polar aprotic organic solvents. Solvents which can preferably be used are ethers, such as diethyl ether, diisopropyl ether, methyl t-butyl ether, methyl t-amyl ether, dioxane, tetrahydrofuran, 1,2-dimethoxyethane, 1,2-diethoxyethane or anisole, and furthermore ketones, such as acetone, butanone, methyl isobutyl ketone or cyclohexanone, and also nitriles, such as acetonitrile, propionitrile, n- or i-butyronitrile or benzonitrile; and moreover amides, such as N,N-dimethylformamide, N,N-dimethylacetamide, N-methylformanilide, N-methylpyrrolidone or hexamethylphosphoric acid triamide; and furthermore esters, such as methyl acetate or ethyl acetate, and also sulphoxides, such as dimethyl sulphoxide, or sulphones, such as sulpholane.

Possible particularly preferred diluents are sulphones, such as sulpholane.

The reaction temperatures can be varied within a substantial range in carrying out the first stage of the process according to the invention. In general, the reaction is carried out at temperatures between 100° C. and 250° C., preferably between 150° C. and 200° C.

Both the first and the second stage of the process according to the invention are in general carried out under normal pressure. However, it is also possible to operate under increased or reduced pressure. In general, pressures between 0.1 bar and 10 bar are used.

Possible add acceptors in carrying out the second stage of the process according to the invention are all the customary inorganic and organic acid-binding agents. Acid-binding agents which can preferably be used are alkaline earth metal or alkali metal hydroxides, carbonates or bicarbonates, such as, for example, sodium hydroxide, potassium hydroxide, sodium carbonate, potassium carbonate, potassium bicarbonate or sodium bicarbonate, as well as tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Bicyclic tertiary amines, such as diazabicyclooctane (DABCO), diazabicyclononene (DBN) or diazabicycloundecene (DBU) can particularly preferably be used.

Possible diluents in carrying out the second stage of the process according to the invention are all the inert organic solvents. Solvents which can preferably be used are aliphatic, alicyclic or aromatic hydrocarbons, such as petroleum ether, hexane, heptane, cyclohexane, methylcyclohexane, benzene, toluene, xylene or decalin, and furthermore halogenated hydrocarbons, such as chlorobenzene, dichlorobenzene, methylene chloride, chloroform, carbon tetrachloride, dichloroethane or trichloroethane, and also ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; and moreover ketones, such as acetone, butanone, methyl isobutyl ketone or cyclohexanone, and additionally nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric acid triamide, and furthermore esters, such as methyl acetate or ethyl acetate, sulphoxides, such as dimethyl sulphoxide, or sulphones, such as sulpholane.

Possible particularly preferred diluents are nitriles, such as acetonitrile, propionitrile or n- or i-butyronitrile.

The reaction temperatures can be varied within a substantial range in carrying out the second stage of the process according to the invention. The reaction is in general carried out at temperatures between 0° C. and 120° C., preferably between 50° C. and 110° C.

In carrying out the first stage of the process according to the invention, in general 2 to 15 mol, preferably 2 to 4 mol, of fluoride are employed per mole of 1,3-dimethyl-5-chloro-pyrazole-4-carbonyl chloride of the formula (II). In detail, a procedure is in general followed in which 1,3-dimethyl-5-chloro-pyrazole-4-carbonyl chloride is added to a solution of the fluoride in a solvent and resulting mixture is heated at the desired temperature until the reaction has ended. Subsequent working up is carried out by customary methods. In general, a procedure is followed in which the reaction mixture is subjected to a fractional distillation under reduced pressure.

In carrying out the second stage of the process according to the invention, in general 1 to 15 mol, preferably 1 to 2 mol, of aniline of the formula (IV) are employed per mole of 1,3-dimethyl-5-fluoro-pyrazole-4-carbonyl fluoride of the formula (III). In detail, a procedure is in general followed in which the components are mixed in any desired sequence and the resulting mixture is stirred at the desired temperature until the reaction has ended. Working up is carried out by customary methods. In general, a procedure is followed in which the reaction mixture is concentrated, the residue which remains is stirred with water and the solid product which precipitates out is filtered off with suction and dried, if appropriate after prior washing.

The 1,3-dimethyl-5-fluoro-pyrazole-4-carboxanilides which can be prepared according to the invention are known as active compounds having fungicidal properties (cf. WO 93-11 117).

The procedure for the process according to the invention is illustrated by the following examples.

PREPARATION EXAMPLES

Example 1

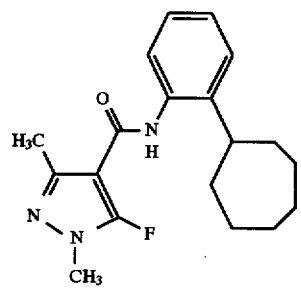

(I-1)

1st stage

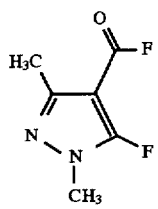
(II)

250 ml of liquid are distilled off from a solution of 437.5 g (7.5 mol) of potassium fluoride in 3750 ml of sulpholane at a temperature of 190° C. under reduced pressure. After the dissolution has cooled to room temperature, 482.6 g (2.5 mol) of 1,3-dimethyl-5-chloro-pyrazole-4-carbonyl chloride are added and the mixture is heated at 190° C. for 11 hours, while stirring. For subsequent working up, the reaction mixture is subjected to fractional distillation over a Vigreux column 30 cm long at a bath temperature of 120° C. under a pressure of 1 mbar. 338.7 g (82.1% of theory) of 1,3-dimethyl-5-fluoro-pyrazole-4-carbonyl fluoride is obtained by this procedure as a first fraction in the form of a liquid which has a boiling point of 68° C. under a pressure of 1 mbar.

2nd stage

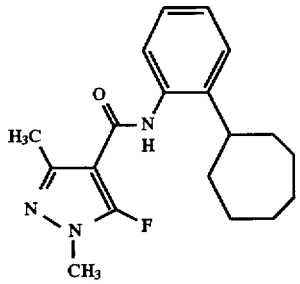
(I-1)

211.7 g of diazabicyclooctane are added to a solution of 264 g (1.26 mol) of 1,3-dimethyl-5-fluoro-pyrazole-4-carbonyl fluoride and 245.6 g (1.26 mol) of 2-cycloheptyl-aniline in 2500 ml of acetonitrile, while stirring, and the mixture is stirred at 70° C. for a further 17 hours. The solvent is then distilled off under reduced pressure and the residue which remains is stirred with 1500 ml of water. The solid which precipitates out by this procedure is filtered off with suction, rinsed with 2000 ml of water and dried by further filtration with suction. The product is washed once more with 1000 ml of cyclohexane and then dried at 50° C. under reduced pressure. 339.1 g (80.9% of theory) of 1,3-dimethyl-5-fluoropyrazole-4-carboxylic acid (2-cycloheptyl)-anilide are obtained in this manner in the form of a solid substance of melting point 146° C.

COMPARISON EXAMPLE

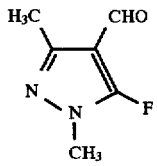

Liquid is distilled off from a solution of 6.6 g (0.114 mol) of potassium fluoride in 100 ml of sulpholane at a temperature of 150° C. under a pressure of 20 mbar for 30 minutes. After the solution has cooled to room temperature, 12.0 g (0.076 mol) of 1,3-dimethyl-5-chloro-pyrazole-4-carbaldehyde are added and the mixture is heated at 190° C. for 5 hours, while stirring. For subsequent working up, the reaction mixture is subjected to fractional distillation over a Vigreux column 30 cm long at a bath temperature of 120° C. under a pressure of 0.4 mbar. 25.6 g of a liquid which has a boiling range from 78° to 90° C. under a pressure of 0.4 mbar is obtained as a first fraction by this procedure. According to analysis by gas chromatography, the distillate comprises 1,3-dimethyl-5-chloro-pyrazole-4-carbaldehyde to the extent of 8.2%, sulpholane to the extent of 80% and 1,3-dimethyl-5-fluoro-pyrazole-4-carbaldehyde to the extent of 10.2%. The yield of 1,3-dimethyl-5-fluoro-pyrazole-4-carbaldehyde is accordingly calculated as 24.2% of theory.

It will be understood that the specification and examples are illustrative but not limitative of the present invention and that other embodiments within the spirit and scope of the invention will suggest themselves to those skilled in the art.

What is claimed is:

1. A process for the preparation of a 1,3-dimethyl-5-fluoro-pyrazole-4-carboxanilide of the formula

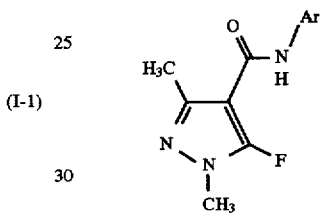

in which

Ar represents optionally substituted phenyl, which process comprises a) reacting in a first stage, 1,3-dimethyl-5-chloro-pyrazole-4-carbonyl chloride of the formula

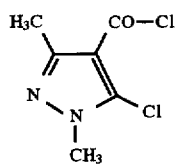

with a fluoride and b) reacting in a second stage, the 1,3-dimethyl-5-fluoro-pyrazole-4-carbonyl fluoride formed in this reaction, of the formula

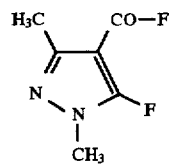

with an aniline of the formula

H₂N—Ar in which

Ar has the abovementioned meaning.

2. A process according to claim 1, wherein the fluoride is an alkali metal fluoride, ammonium fluoride or a phosphonium fluoride.

3. A process according to claim 1, wherein the aniline is a compound in which

Ar represents a grouping of the formula

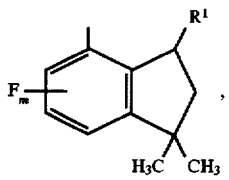

in which
m represents 0 or 1 and
R¹ represents hydrogen or methyl,
or
Ar represents a grouping of the formula

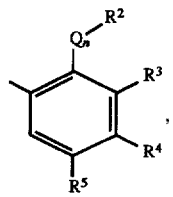

in which
n represents 0 or 1,
Q represents alkylene having 1 to 3 carbon atoms, alkenylene having 2 or 3 carbon atoms or alkinylene having 2 or 3 carbon atoms, or represents a grouping of the formula —(CH$_2$)$_t$—CH=, in which
t represents the numbers 0, 1, 2 or 3 and the —(CH$_2$)$_t$-unit is bonded to the phenyl ring,
or represents a grouping of the formula —(CH$_2$)$_p$—Y—(CH$_2$)$_r$—, in which
p and r independently of one another represent the numbers 0, 1 or 2 and
Y represents oxygen or sulphur, the —(CH$_2$)$_p$-unit in each case being bonded to the phenyl ring,
R² represents cycloalkyl having 3 to 12 carbon atoms which is optionally monosubstituted or polysubstituted in an identical or different manner by alkyl having 1 to 8 carbon atoms, alkoxy having 1 to 8 carbon atoms, halogen and/or cyano, or represents cycloalkenyl having 3 to 12 carbon atoms which is optionally monosubstituted or polysubstituted in an identical or different manner by alkyl having 1 to 8 carbon atoms, alkoxy having 1 to 8 carbon atoms, halogen and/or cyano, or
represents bicycloalkyl having 6 to 12 carbon atoms which is optionally monosubstituted or polysubstituted in an identical or different manner by alkyl having 1 to 8 carbon atoms, alkoxy having 1 to 8 carbon atoms, halogen and/or cyano, or
represents oxacycloalkyl having 2 to 12 carbon atoms which is optionally monosubstituted or polysubstituted in an identical or different manner by alkyl having 1 to 8 carbon atoms, alkoxy having 1 to 8 carbon atoms, halogen and/or cyano, or
represents oxacycloalkenyl having 4 to 12 carbon atoms which is optionally monosubstituted or polysubstituted in an identical or different manner by alkyl having 1 to 8 carbon atoms, alkoxy having 1 to 8 carbon atoms, halogen and/or cyano, or represents thiacycloalkyl having 3 to 12 carbon atoms, which is optionally monosubstituted or polysubstituted in an identical or different manner by alkyl having 1 to 8 carbon atoms, alkoxy having 1 to 8 carbon atoms, halogen and/or cyano, or
represents thiacycloalkenyl having 4 to 12 carbon atoms which is optionally monosubstituted or polysubstituted in an identical or different manner by alkyl having 1 to 8 carbon atoms, alkoxy having 1 to 8 carbon atoms, halogen and/or cyano, or
represents azacycloalkyl having 2 to 12 carbon atoms which is optionally monosubstituted or polysubstituted in an identical or different manner by alkyl having 1 to 8 carbon atoms, alkoxy having 1 to 8 carbon atoms, halogen and/or cyano,
the saturated or unsaturated ring in each case being divalent if —Q—R² represents —(CH$_2$)$_t$—CH=, and
R³, R⁴ and R⁵ independently of one another represent hydrogen, halogen, cyano, alkyl having 1 to 6 carbon atoms, alkenyl having 2 to 6 carbon atoms, alkinyl having 2 to 6 carbon atoms, alkoxy having 1 to 4 carbon atoms, alkylthio having 1 to 4 carbon atoms, cycloalkyl having 3 to 6 carbon atoms or halogenomethoxy.

4. A process according to claim 1, wherein the aniline is a compound, in which

Ar represents a grouping of the formula

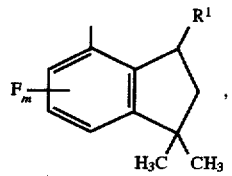

in which
m represents 0 or 1 and
R¹ represents hydrogen or methyl
or
Ar represents a grouping of the formula

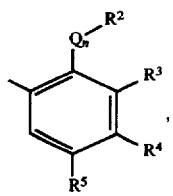

in which
Q represents straight-chain or branched alkylene having 1 to 3 carbon atoms, alkenylene having 2 or 3 carbon atoms or alkinylene having 2 or 3 carbon atoms, or represents a grouping of the formula —(CH$_2$)$_t$—CH=, in which
t represents the numbers 0, 1 or 2, the —(CH$_2$)$_t$-unit in each case being bonded to the phenyl ring,
or represents a grouping of the formula —(CH$_2$)$_p$—Y—(CH$_2$)$_r$—, in which
p and r independently of one another represent the numbers 0, 1 or 2 and
Y represents oxygen or sulphur,
the —(CH$_2$)$_p$-unit in each case being bonded to the phenyl ring, n represents the numbers 0 or 1, R² represents cycloalkyl having 3 to 8 carbon atoms which is optionally monosubstituted to tetrasubstituted in an identical or different manner by alkyl having 1 to 4 carbon atoms, alkoxy having 1 to 4 carbon atoms, fluorine, chlorine, bromine and/or cyano, or represents cycloalkenyl having 3 to 8 carbon atoms which is optionally monosubstituted to tetrasubstituted in an identical or different manner by alkyl having 1 to 4 carbon atoms, alkoxy having 1 to 4 carbon atoms, fluorine, chlorine, bromine and/or cyano, or represents bicycloalkyl having 6 to 10 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, or represents oxacycloalkyl having 2 to 7 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, or represents oxacycloalkenyl having 4 to 7 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, or represents thiacycloalkyl having 3 to 7 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, or represents thiacycloalkenyl having 4 to 7 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, or represents azacycloalkyl having 2 to 7 carbon atoms which is optionally monosubstituted to trisubstituted in an identical or different manner by alkyl having 1 to 4 carbon atoms, alkoxy having 1 to 4 carbon atoms, fluorine, chlorine, bromine and/or cyano, the ring in the abovementioned radicals in each case being divalent if the grouping —Q—R² represents —(CH₂)ₙ—CH=, and R³, R⁴ and R⁵ independently of one another represent hydrogen, fluorine, chlorine, bromine, cyano, alkyl having 1 to 4 carbon atoms, alkenyl having 2 to 4 carbon atoms, alkinyl having 2 to 4 carbon atoms, methoxy, ethoxy, methylthio, ethylthio, cyclopropyl, cyclopentyl, cyclohexyl, fluoromethoxy, difluoromethoxy, trifluoromethoxy, chloromethoxy, dichloromethoxy or trichloromethoxy.

5. A process according to claim 1, wherein the aniline is a compound, in which

Ar represents a grouping of the formula

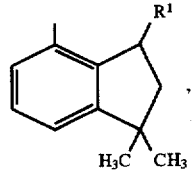

in which

R¹ represents hydrogen or methyl, or

Ar represents a grouping of the formula

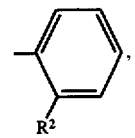

in which

R² represents cyclopentyl, cyclohexyl, cycloheptyl or bicyclo-[2,2,1]heptyl.

6. A process according to claim 1, which comprises a) reacting in a first stage, 1,3-dimethyl-5-chloropyrazole-4-carbonyl chloride with potassium fluoride and b) reacting in a second stage, the 1,3-dimethyl-5-fluoropyrazole-4-cabonyl fluoride thus obtained with 2-cycloheptyl-aniline.

7. A process according to claim 1, wherein a) the reaction in the first stage is carried out at a temperature between 100° C. and 200° C. and b) the reaction in the second stage is carried out at a temperature between 0° C. and 120° C.

8. A process according to claim 1, wherein in the reactions in the first and second stage are carried out in the presence of a diluent.

9. A process according to claim 1, wherein the reaction in the second stage is carried out in the presence of an acid acceptor.

* * * * *